United States Patent
Von Oepen et al.

[11] Patent Number: 5,916,264
[45] Date of Patent: Jun. 29, 1999

[54] STENT GRAFT

[75] Inventors: Randolf Von Oepen, Hirrlingen; Nikolaus Reifart, Eppstein, both of Germany

[73] Assignee: Jomed Implantate GmbH, Rangendingen, Germany

[21] Appl. No.: 09/048,358

[22] Filed: Mar. 26, 1998

[30] Foreign Application Priority Data

May 14, 1997 [DE] Germany ............... 197 20 115

[51] Int. Cl.⁶ ................................................. A61F 2/06
[52] U.S. Cl. .................................. 623/1; 623/12
[58] Field of Search ............................ 623/1, 11, 12

[56] References Cited

U.S. PATENT DOCUMENTS

| | | | |
|---|---|---|---|
| 5,064,435 | 11/1991 | Porter | 623/12 |
| 5,380,328 | 1/1995 | Morgan | 606/70 |
| 5,383,927 | 1/1995 | De Goicoechea et al. | |
| 5,613,982 | 3/1997 | Goldstein | |
| 5,632,778 | 5/1997 | Goldstein | |
| 5,645,559 | 7/1997 | Hachtman | 606/198 |
| 5,667,523 | 9/1997 | Bynon | 606/198 |
| 5,723,003 | 3/1998 | Winston | 623/1 |
| 5,843,120 | 12/1998 | Israel | 623/1 |
| 5,858,556 | 1/1999 | Eckert | 623/1 |

FOREIGN PATENT DOCUMENTS

WO 97/24081  8/1997  WIPO .

*Primary Examiner*—Michael J. Milano
*Attorney, Agent, or Firm*—Michael J. Striker

[57] ABSTRACT

A stent graft has two coaxially arranged, radially expandable stents, and a flexible, stretchable material layer arranged between the stents. Both stents are directly connected with one another in their end regions and the material layer is formed as a fabric band wound around an inner stent.

11 Claims, 1 Drawing Sheet

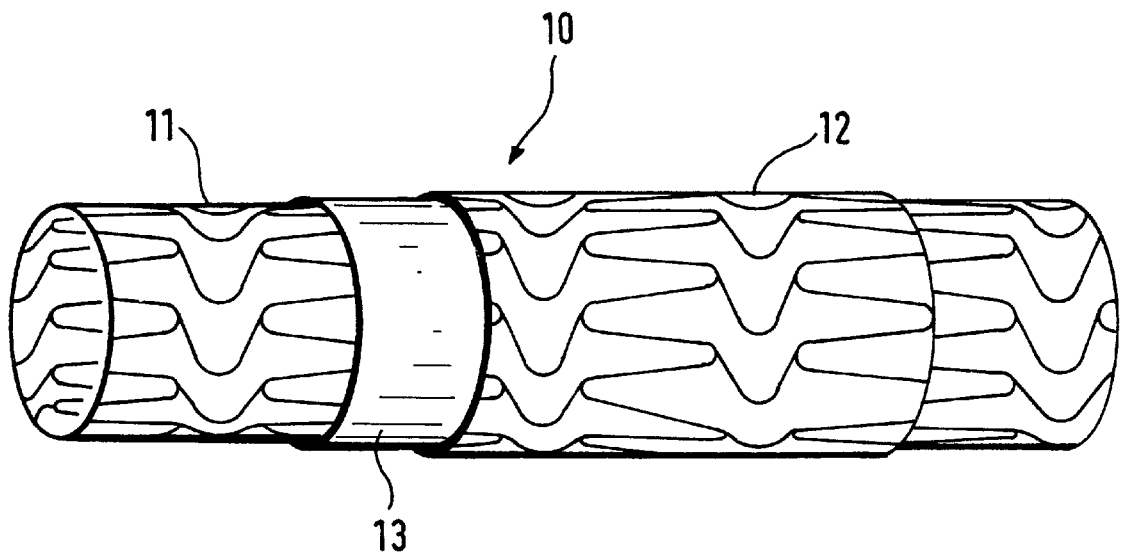

STENT GRAFT

BACKGROUND OF THE INVENTION

The present invention relates to a stent graft.

More particularly, it relates to a stent graft which is used for supporting of vessels, in particular in the case of aneurisms and also in the case of labile or brittle or thrombotic vessels.

Conventional stent grafts are composed as a rule of a radially extending stent which is produced for example by a laser cutting from metal tubes and a coating which is sewn on it and composed of a fabric or a foil. The coating has the objective to prevent a blood passage or a passage of blood components or deposits through the wall of the stent graft as well as a growing of the fabric through the wall into the interior of the stent graft. Thereby it is also guaranteed that the vessel wall is unloaded from blood pressure and at the implementation point of the stent graft no embolie can occur.

In the conventional stents knots are formed because of a fixed sewing of the coating to the stent. They lead to whirling in open through flow of the vessel with the danger of a rhombus formations. When the coating is composed of knitted or woven fabric, it must be folded around the stent. A fold-free tensioning of the coating during dilatation of the stent is therefore not always guaranteed.

SUMMARY OF THE INVENTION

Accordingly, it is an object of present invention to provide a stent graft which avoids the disadvantages of the prior art.

In keeping with these objects and with others which will become apparent hereinafter, one feature of present invention resides, briefly stated, in a stent graft which has two coaxially arranged radial extending stents, and between the both stents a flexible, stretchable material layer is provided, for example a flexible and stretchable biological fabric.

In the inventive stent graft sewing of the material layer on a stent can be dispensed with, since the material layer between the coaxial stents is clamped. Moreover, the material layer during insertion of the stent into the vessel is protected from injuries. Because of the flexible and stretchable properties of the material layer, it can be radially extended together with the both stents on the implantation location.

For preventing an opposite-side displacement of both stents during the reinsertion, the both stents can be connected with one another punctually in their end regions. For this purpose, different methods can be used. For example, both stents can be welded with one another, pressed or glued.

The material layer can be formed of a hose-shaped (flexible-tube-shaped) element composed of a foil or a fabric from a body-compatible material, or of a biological fabric.

The material layer can however be composed also of a foil or fabric band which is wound around the inner stent. Thereby an especially rational manufacture of the stent graft is possible.

The material for the intermediate layer can be for example polythetrafluorethylene, polyethylenteraphthalate or biological materials with autologous or homologous veins or arteries.

The preliminarily expanded polythetrafluorethylene has special advantages, since this material has a fibril structure. Thereby, the growth of the wire graft in the vessel wall is favorable. Thereby, a fixed compound between the vessel and the stent graft is produced in time.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

The single FIGURE of the drawings shows a partially sectioned perspective view of a stent graft in accordance with the present invention.

DESCRIPTION OF PREFERRED EMBODIMENTS

A stent graft in accordance with the present invention is identified with reference numeral 10. It is composed of two coaxial stents 11 and 12. An expandable material layer 13 is arranged between the coaxial stents 11 and 12. The layers 13 can be also produced from a body-compatible synthetic plastic foil or synthetic plastic fabric. However, the utilization of other body-compatible or biological materials is possible as well. In the shown example the material layer 13 extends only over the part of the length of the stent graft 10.

The material layer 13 overlaps only one part of the stents 11, 12. The both stents 11, 12 can be connected with one another in their end regions punctually, by a plurality of points.

The material layer 13 can be formed by a foil or fabric band wound around the inner stent. It can be composed of polythetrafluorethylene or polyethylenteraphthalate. Also, can be composed of a biological material of autologous or homologous origin.

It will be understood that each of the elements described above, or two or more together, may also find a useful application in other types of constructions differing from the types described above.

While the invention has been illustrated and described as embodied in stent graft, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A stent graft, comprising two coaxially arranged, radially expandable stents, both said stents being directly connected with one another in their end regions; and a flexible, stretchable material layer arranged between said stents, said material layer being formed as a fabric band which is wound around an inner one of said stents.

2. A stent graft as defined in claim 1, wherein said material layer overlaps only a part of said stents.

3. A stent graft as defined in claim 1, wherein both said stents are punctually connected with one another in their end regions.

4. A stent graft as defined in claim 1 wherein said material layer is formed as a hose-shaped element composed of a foil.

5. A stent graft as defined in claim 1, wherein said material layer is formed as a hose-shaped element composed of a fabric.

6. A stent graft as defined in claim 1, wherein said material layer is formed as a foil band which is wound around an inner one of said stents.

7. A stent graft as defined in claim 1, wherein said material layer is composed of polythetrafluorethylene.

8. A stent graft is defined in claim 1, wherein said material layer is formed of polyethylenteraphthalate.

9. A stent graft as defined in claim 1, wherein said material layer is composed of a biological material.

10. A stent graft as defined in claim 1, wherein said biological material is an autologous material.

11. A stent graft as defined in claim 9 wherein said biological material is a homologous material.

\* \* \* \* \*